United States Patent

Callinan et al.

[11] Patent Number: 6,030,355
[45] Date of Patent: Feb. 29, 2000

[54] ORTHOPEDIC SUPPORT MATERIAL CONTAINING A SILICATE

[75] Inventors: Andrew J. Callinan, Robbinsdale, Minn.; Kimberly D. Windom, Ames, Iowa

[73] Assignee: 3M Innovative Properties Company, St. Paul, Minn.

[21] Appl. No.: 08/969,206

[22] Filed: Nov. 12, 1997

[51] Int. Cl.[7] .................................................... A61F 5/00
[52] U.S. Cl. .................................... 602/6; 602/8; 602/41
[58] Field of Search ...................................... 602/41, 50, 8

[56] References Cited

U.S. PATENT DOCUMENTS

| | | | |
|---|---|---|---|
| 4,411,262 | 10/1983 | von Bonin et al. | 128/90 |
| 4,416,694 | 11/1983 | Stevenson et al. | 106/84 |
| 4,484,949 | 11/1984 | Potter et al. | 106/85 |
| 4,502,479 | 3/1985 | Garwood et al. | 128/90 |
| 4,667,661 | 5/1987 | Scholz et al. | 128/90 |
| 4,668,563 | 5/1987 | Buese et al. | 428/230 |
| 4,841,958 | 6/1989 | Ersfeld et al. | 128/90 |
| 4,940,047 | 7/1990 | Richter et al. | 128/90 |
| 4,983,218 | 1/1991 | Mascioli | 106/600 |
| 5,336,315 | 8/1994 | Cuscurida et al. | 106/633 |
| 5,342,291 | 8/1994 | Scholz et al. | 602/41 |
| 5,423,735 | 6/1995 | Callinan et al. | 602/8 |
| 5,512,354 | 4/1996 | Scholz et al. | 428/231 |

FOREIGN PATENT DOCUMENTS

| | | |
|---|---|---|
| 14 16 954A | 2/1969 | Germany . |
| 949469A | 2/1964 | United Kingdom . |
| 1 554 554 | 10/1979 | United Kingdom . |
| 1 554 555 | 10/1979 | United Kingdom . |
| 2 090 823A | 7/1981 | United Kingdom . |

OTHER PUBLICATIONS

*Encyclopedia of Chemical Technology*, vol. 18, 2nd ed., Copyright 1969, John Wiley & Sons, Inc. pp. 134–139.

"Sodium Silicates Hydrated and Anhydrous Powders", Industrial Chemicals Division, The PQ Corporation, Valley Forge, PA.

"Britesil Hydrous Polysilicates", Industrial Chemicals Division, The PQ Corporation, Valley Forge, PA.

*Primary Examiner*—John G. Weiss
*Assistant Examiner*—Kelvin Hart
*Attorney, Agent, or Firm*—Eloise J. Maki

[57] ABSTRACT

The present invention provides a silicate-containing composition for use in an orthopedic support material. The silicate-containing composition includes a water-soluble silicate, wherein at least about 1 part of the water-soluble silicate is soluble in about 6 parts water at 25° C. Preferably, the water-soluble silicate has the formula $SiO_2/M_2O$ wherein M is Li, Na, K, or $NR_4$, wherein each R is independently hydrogen or a $(C_1-C_{10})$organic group.

29 Claims, 1 Drawing Sheet

ORTHOPEDIC SUPPORT MATERIAL CONTAINING A SILICATE

FIELD OF THE INVENTION

The present invention relates to orthopedic support materials made of a substrate impregnated with a hardenable silicate-containing composition. The invention also relates to methods of making the support materials, methods of making casts from the support materials, and the resulting orthopedic casting products.

BACKGROUND OF THE INVENTION

Many different orthopedic casting materials have been developed for use in the immobilization of broken or otherwise injured body limbs. Some of the first casting materials developed for this purpose involved the use of plaster of Paris bandages consisting of mesh fabric (e.g., cotton gauze) with plaster (e.g., calcium sulfate hemihydrate) incorporated into the openings and onto the surface of the mesh fabric. Plaster of Paris casts, however, have a number of attendant disadvantages, including a low strength-to-weight ratio, resulting in a finished cast that is very heavy and bulky. In addition, plaster of Paris casts develop their strength over a relatively long period of time. This makes it necessary to avoid weight bearing situations for up to 48 hours. Furthermore, plaster of Paris casts typically disintegrate in water. This makes it necessary to avoid bathing, showering, or other activities involving contact with water.

Polycarboxylate cement casting materials that contain finely divided calcium aluminosilicate glass and calcium fluoroaluminosilicate glass are known. The calcium aluminosilicate or calcium fluoroaluminosilicate glasses are combined with a polycarboxylic acid, which when mixed with water set to form a solid mass. Such glass-containing polycarboxylate cements are generally expensive to make and often have slow set-up times (e.g., greater than about 10 minutes). Additionally, fluoroaluminosilicate glasses are undesirable because they are very expensive to manufacture due to the presence of fluorine, which requires strict environmental controls.

More recently, orthopedic casting tapes have been produced using curable resins coated or impregnated onto a substrate. Typically, the casting tape is stored as a roll in a water-impermeable storage pouch until needed for use. When needed, the roll of tape is removed from the pouch and contacted with water. Generally, the casting tape includes a water-curable resin Thus, shortly after the tape is dipped in water, the resin will begin to cure and the tape harden. The medical practitioner applies the casting tape to a patient immediately after it has been soaked with water. Generally, resin materials are chosen that begin to cure immediately after being dipped in water, and that will set (i.e., harden) sufficiently to resist passive motion in a joint (e.g., a wrist or ankle) in about 3 minutes to about 5 minutes, and to be weight bearing within about 30 minutes.

Typical resin coatings utilized in conventional orthopedic casting systems include isocyanate-functional urethane prepolymers. Other known systems include nonisocyanate alkoxysilane-terminated urea and/or urethane prepolymers. Generally, such resin coatings also include catalysts to facilitate reaction with water. Lubricants may also be used, e.g., to facilitate unrolling, application, and molding. Furthermore, defoaming agents may be used to maintain porosity while carbon dioxide is evolved during the curing process.

Typical substrates upon which the above resin coatings are applied to produce an orthopedic casting tape are fabrics prepared from glass and/or synthetic fibers. Fiberglass or other high modulus fibers contribute significant strength to the cured resin substrate composite as well as provide a reservoir for the resin during storage and end-use application of the casting tape. Nonglass low modulus substrates generally provide for a lower weight and more radiolucent cast. With most nonglass substrates the strength is limited by the amount of resin that can be held by the substrate. High resin loading with materials known to date must generally be avoided, however, to prevent excessive heat build-up in the cast while it is in its early stages of cure, i.e., during hardening, as a result of the exotherm produced in the above resins.

A need still exists for a hardenable composition that can be used in a wide variety of orthopedic support materials, whether used in combination with a fiberglass substrate or a nonglass low modulus substrate, particularly one that is more economical and/or environmentally friendly than conventional compositions and can withstand exposure to water once hardened.

SUMMARY OF THE INVENTION

The present invention provides a hardenable silicate-containing medical dressing capable of immobilizing and/or supporting a body part, i.e., as an orthopedic support material. This hardenable dressing can be used in tape, sheet, film, slab, or tubular form to prepare orthopedic casts, splints, braces, supports, protective shields, orthotics, and the like. Additionally, other constructions in prefabricated shapes can be used.

In a preferred embodiment, the hardenable orthopedic support material of the present invention is composed of a substrate coated or impregnated with a hardenable silicate-containing composition. The hardenable silicate-containing composition of the present invention consists primarily of one or more water-soluble silicates (also referred to herein as "soluble silicate").

A preferred embodiment of the present invention is an orthopedic support material comprising a substrate and a hardenable composition comprising a water-soluble silicate, wherein at least about 1 part of the water-soluble silicate is soluble in about 6 parts water at 25° C. Preferably, the water-soluble silicate has the formula $SiO_2/M_2O$ wherein M is Li, Na, K, or $NR_4$, wherein each R is independently hydrogen or a $(C_1-C_{10})$organic group. Preferably, each R is independently hydrogen or an organic group selected from the group of an allyl group, an aryl group, an aralkyl group, and an alkaryl group.

Another preferred embodiment of the present invention is an orthopedic support material comprising a substrate and a hardenable composition consisting essentially of a water-soluble silicate, wherein at least about 1 part of the water-soluble silicate is soluble in about 6 parts water at 25° C.

Yet another preferred embodiment of the present invention is an orthopedic support material comprising a substrate and a hardenable composition comprising: a water-soluble silicate having the formula $SiO_2/M_2O$ wherein M is Li, Na, K, or $NR_4$, wherein each R is independently hydrogen or a $(C_1-C_{10})$organic group, and wherein at least about 1 part of the water-soluble silicate is soluble in about 6 parts water at 25° C.; and a hardening agent. Preferably, the hardening agent is selected from the group of inorganic acids, organic acids, esters, anhydrides, alkylene carbonates, and salts, derivatives, and mixtures thereof. More preferably, the hardening agent is an allylene carbonate.

The composition can optionally include an effective amount of one or more other adjuvants such as fillers, polymeric toughening agents, binding agents, drying agents, hydrophobic materials, antifoaming agents, lubricants, stabilizers, tackifiers, pigments, dyes, or fragrances. Preferably, the adjuvant is a filler, a polymeric toughening agent, a drying agent, or mixtures thereof Suitable substrates onto which the composition is coated or impregnated include knit, woven, and nonwoven fabrics as well as rigid foams and other porous materials. The substrate is preferably coated or impregnated with the hardenable silicate-containing composition in an amount of about 0.5 time to about 20 times the weight of the substrate. Generally, the composition is within some of the spaces in the substrate between the fibers or filaments. Upon hardening, the composition generally becomes bonded, physically or chemically, to the substrate, forming a hardened silicate composite material.

The hardenable silicate-containing composition of the present invention is typically in the form of solid particulate material (often, in the form of a finely divided powder), which can be slightly moist, or a nonaqueous paste or slurry. Upon exposure of the composition to water (usually by immersing it in water), the composition hardens on the substrate to form a hardened silicate composite. In another embodiment, a substrate can be coated or impregnated with an aqueous solution or dispersion of the hardenable silicate-containing composition, which upon removal of the water (as by evaporation, for example), hardens to form a hardened silicate composite.

Thus, the present invention provides a method of preparing an orthopedic support material. The method includes the steps of: providing a substrate; applying a hardenable composition comprising a water-soluble silicate to the substrate, wherein at least about 1 part of the water-soluble silicate is soluble in about 6 parts water at 25° C.; and allowing the hardenable composition to harden.

The present invention also provides a method of immobilizing a body part. The method includes the steps of: providing an orthopedic support material comprising a substrate and a hardenable composition comprising a water-soluble silicate, wherein at least about 1 part of the water-soluble silicate is soluble in about 6 parts water at 25° C.; applying the orthopedic support material to a body part; applying water to the orthopedic support material to harden the hardenable composition; and allowing the hardenable composition to harden. The step of applying water can occur either before or after the step of applying the orthopedic support material to a body part.

The present invention provides another method of immobilizing a body part. This method includes the steps of: providing an orthopedic support material comprising a substrate and a hardenable composition comprising water and a water-soluble silicate, wherein at least about 1 part of the water-soluble silicate is soluble in about 6 parts water at 25° C.; applying the orthopedic support material to a body part; and removing at least part of the water from the orthopedic support material to harden the hardenable composition.

DEFINITIONS

As used herein the terms "orthopedic support material" or "orthopedic casting material" are used to encompass a wide variety of dressings comprising a hardenable silicate-containing composition; "cast" or "support" are used to include a wide variety of hardened orthopedic support structures; "an effective amount" of an adjuvant means an amount sufficient to provide one or more of the benefits of such an adjuvant, as described herein; "impregnate" refers to a condition in which the composition is thoroughly intermingled with, and in surrounding relation to, the fibers or filaments of the substrate; and "hardenable" means that the composition is capable of hardening to a rigid, semi-rigid, or flexible structure on exposure to water, and the resultant material is referred to as "hardened."

The term "organic group" includes a hydrocarbon group that is classified as an aliphatic group, cyclic group, or combination of aliphatic and cyclic groups (e.g., alkaryl and aralkyl groups). Such organic groups may include heteroatoms (e.g., nitrogen, oxygen, sulfur) or functional groups (e.g., carbonyl groups). In the context of the present invention, the term "aliphatic group" means a saturated or unsaturated linear or branched hydrocarbon group, including alkyl alkenyl, and alkynyl groups, for example, which may optionally include heteroatoms or functional groups. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

Substitution is also possible on the compounds of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "ally group" is intended to include not only pure open chain saturated hydrocarbon alkyl substituents, such as methyl, ethyl, propyl, t-butyl, and the like, but also alkyl substituents bearing further substituents known in the art, such as hydroxy, for example. On the other hand, the phrase "allyl moiety" is limited to the inclusion of only pure open chain saturated hydrocarbon alkyl substituents, such as methyl, ethyl, propyl, t-butyl, and the like.

DETAILED DESCRIPTION OF PREFERRED EMBODIMENTS

Figure 1:
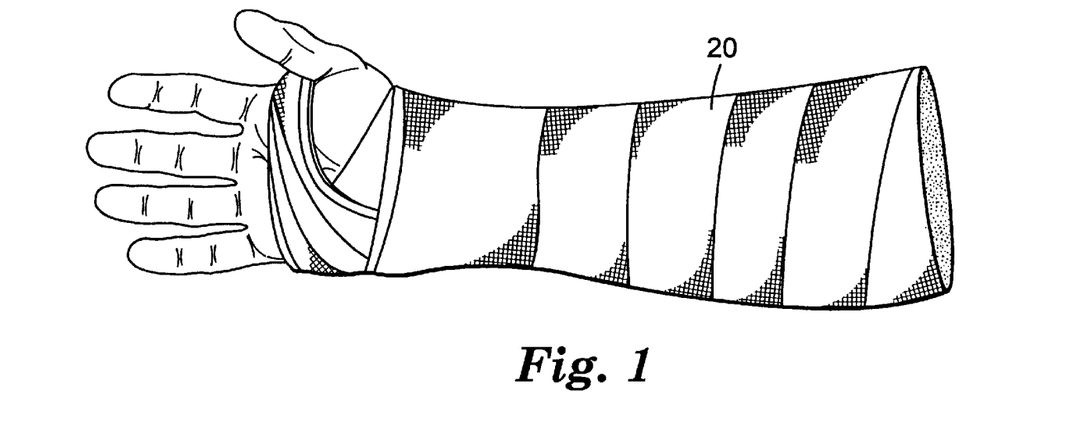
FIG. 1 is a schematic representation of a casting material 20 of the present invention shown wrapped in position for hardening.
Figure 2:
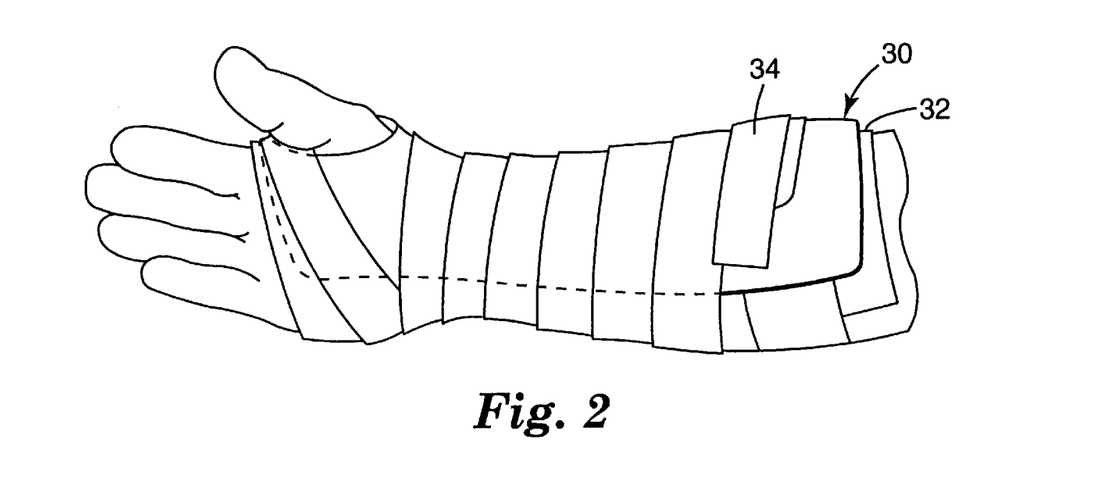
FIG. 2 is a schematic representation of a casting material of the present invention shown wrapped as a splint 30. An optional underpadding 32 and an optional overwrap 34 are also depicted.

Suitable compositions for use in the orthopedic casting materials (e.g., tapes) of the present invention preferably have one or more of the following properties: substantial storage life; low toxicity; reasonable work life such that there is a reasonable period of time in which to mold the material to the limb; fast hardening rate such that the composition hardens to form a weight-bearing cast within a period of about 30 minutes to several hours; hardenable to a relatively strong, tough, and long lasting cast such that the cast is sufficiently strong (whether flexible, semi-rigid, or rigid) to support a fractured limb; hardenable to a substantially waterproof cast (i.e., a cast that will not soften to the extent that the cast breaks down during normal use or delaminate upon contact with water after hardening); hardenable to form a cast that can be readily removed without discomfort to the patient; hardenable with little shrinkage of the cast; nontacky upon contact with water; minimal or nonoffensive smell; free of offensive or noxious organic solvents; and reasonable flexibility in the uncured state such that the material readily assumes the shape of the limb during application. The present invention concerns the development and identification of such a composition.

Hardenable compositions for use in orthopedic support materials according to the present invention comprise a water-soluble silicate. That is, they include one or more water-soluble silicates. They can also include one or more hardening agents and/or other optional adjuvants. The hardenable silicate-containing compositions are typically in the form of a solid particulate material (often, in the form of a powder), which can be moist, or can be in the form of a nonaqueous paste or slurry. Upon contact with water, the composition hardens to form a hardened silicate composite. Alternatively, a substrate can be coated or impregnated with an aqueous solution or dispersion of the silicate-containing composition. Upon at least partial removal of the water, the composition hardens to form a hardened silicate composite.

Preferred hardenable compositions include an effective amount of a hardening agent that accelerates the hardening of the composition. Such hardenable compositions are described in, for example, U.S. Pat. Nos. 5,336,315 (Cuscurida et al.), and 4,983,218 (Mascioli) and 4,416,694 (Foseco Int. Ltd.) which are incorporated by reference. They are used as binders to stabilize soil and to agglomerate particulate matter (earth, clay, sand, or soil) in the production of foundry molds. They are also used in combination with a foaming agent to fill cavities in mines and for heat and sound insulation.

Water-Soluble Silicates

Suitable hardenable silicate-containing compositions for use in the orthopedic support materials of the present invention include water-soluble silicates. Such compounds are macroscopically soluble in water at room temperature. By this it is meant that at least about 1 part of the water-soluble silicate is macroscopically soluble in about 6 parts water at 25° C. It is noted that suitable water-soluble silicates include compounds that appear cloudy to the eye when mixed with water under these conditions. As used herein, a silicate is soluble when it effectively becomes a macroscopically homogeneous mixture with water and is thus capable of undergoing the hardening process described herein. Preferably, such compounds are readily soluble in water such that at least about 1 part of the water-soluble silicate dissolves in about 6 parts water at 25° C. in less than about 20 minutes, preferably, in less than about 5 minutes, and more preferably, in less than about 1 minute.

Suitable water-soluble silicates (also referred to herein as "soluble silicates") include alkali metal and quaternary ammonium silicates or polysilicates. Soluble silicates are described in the *Encyclopedia of Chemical Technology*, 18, $2^{nd}$ ed., pages 134–139, John Ailey & Sons, Inc., 1969, which is incorporated herein by reference. Soluble silicates are often characterized by their weight ratio of silica to metal (or ammonium) oxide. Preferred soluble silicates have the following formula: $SiO_2/M_2O$ wherein M is Li, Na, K, or $NR_4$, wherein R is hydrogen or a $(C_1-C_{10})$ organic group. Preferably, such water-soluble silicates have a weight ratio of silica to metal (or ammonium) oxide of at least about 0.20/1, more preferably, at least about 1/1, and most preferably, at least about 1.6/1. Preferably, such water-soluble silicates have a weight ratio of silica to metal (or ammonium) oxide of no greater than about 20/1, more preferably, no greater than about 10/1, and most preferably, no greater than about 3.3/1.

Preferably, each R is independently hydrogen or an organic group selected from the group of an alkyl group, an aryl group, an aralkyl group, and an alkaryl group. Preferred alkyl groups are alkyl moieties (i.e., unsubstituted alkyl groups) and alkyl groups containing one or more O, N, or S atoms or hydroxy substitution. More preferably, each R is independently hydrogen or an organic group selected from the group of an allyl moiety, an alkyl group interrupted with one or more O, N, or S atoms, a hydroxyalkyl group, an aryl group, an arallyl group, and an alkaryl group.

Preferred water-soluble silicates are sodium silicates and potassium silicates primarily because they have high water solubility, are lower in cost, and are more widely available. These include sodium silicate and potassium silicate characterized by having a weight ratio $SiO_2/Na_2O$ or $SiO_2/K_2O$ of about 1.6/1 to about 3.3/1. Typically, the higher the weight ratio of $SiO_2$ to $M_2O$, the lower the water solubility. Soluble silicates with ratios at the high end of this range may be useful when warm water is used to harden the materials.

Examples of suitable water-soluble silicates include those available under the trade designations "BRITESIL" C24 hydrous sodium polysilicate powder with a $SiO_2/Na_2O$ weight ratio of 2.4/1, "GD" sodium silicate powder with a $SiO_2/Na_2O$ weight ratio of 2/1, and "KASOLV" potassium silicate powder with a $SiO_2/K_2O$ weight ratio of 2/1, all of which are available from the PQ Corporation, Valley Forge, Pa. Aqueous solutions of water-soluble silicates are available under the trade designation "TEX-SIL" BP-42 (42% solids) from Chemical Products Corp., Cartersville, Ga.

One or more of the water-soluble silicates can be used in the compositions of the present invention. Preferably, the water-soluble silicates are used in the compositions of the present invention in an amount of at least about 10 percent by weight (wt-%), more preferably, at least about 30 wt-%, and most preferably, at least about 45 wt-%, based on the total weight of the hardenable composition. Preferably, the water-soluble silicates are used in the compositions of the present invention in an amount of no greater than about 90 wt-%, more preferably, no greater than about 75 wt-%, and most preferably, no greater than about 60 wt-%.

Hardening Agents

Suitable hardening agents for use in the orthopedic support materials of the present invention include a compound, which, when present in sufficient quantity, will initiate and/or facilitate the hardening of the silicate-containing composition. Typically, this occurs upon at least partial removal of water. Preferably, the hardening agents are those compounds that initiate and/or facilitate hardening of the orthopedic support material but permit sufficient worldng time for the per-son applying the dressing before it hardens into a cast. They are preferably soluble in water to an extent sufficient to accelerate hardening.

Suitable hardening agents include, but are not limited to, inorganic acids, organic acids, esters, and anhydrides, as well as alkylene carbonates, in addition to salts, derivatives, and mixtures thereof Suitable hardening agents are disclosed, for example, in U.S. Pat. Nos. 5,336,315

(Cuscurida et al.), 4,983,218 (Mascioli), and 4,416,694 (Foseco Int. Ltd.), which are incorporated herein by reference. Examples of preferred hardening agents include, but are not limited to, sodium bicarbonate; carboxylic acids, such as citric acid, and polymeric carboxylic acids, such as alginic acid; esters and polyesters, such as triacetin (glycerol triacetate); anhydrides and polyanhydrides, such as phthalic anhydride, succmic anhydride, and "GANTREZ" AN-139 methyl vinyl ether/maleic anhydride copolymer (available from International Specialty Products, Lambard, Ill.); alkylene carbonates and polycarbonates, such as ethylene, propylene, butylene, and glyceryl carbonates and polyester polycarbonates as disclosed in U.S. Pat. No. 5,336,315 (Cuscurida et al.); and derivatives and combinations thereof Particularly preferred hardening agents are the alkylene carbonates.

In the case of glyceryl carbonate, it may be beneficial to increase its molecular weight by reacting the free hydroxyl group with epoxy or isocyanate functional compounds. For example, the reaction of isocyanatopropyltriethoxy silane with glycerol carbonate would yield a hardening agent with alkoxysilane functionality. Hydrolysis of this adduct would yield a silanol functional compound that could potentially react with the hardenable silicates of the present invention. By varying the selection of the type and amount of a preferred hardening agent used with a particular soluble silicate, the set time and early strength of the cast may be controlled.

Particularly preferred hardening agents of the present invention include alkylene carbonates, including ethylene carbonate (a solid at room temperature), propylene carbonate, and mixtures thereof A 50:50 (by weight) mixture of propylene carbonate and ethylene carbonate is available under the trade designation "JEFFSOL" EC-50 from Huntsman Corp., Houston, Tex. Having the alkylene carbonate or other hardening agent in solid form may beneficially enhance product stability.

One or more hardening agents can be used in any one composition of the present invention. If a hardening agent is used, it is used in an amount effective to accelerate hardening such that there is a reasonable period of time in which to mold the material to the limb yet form a weight-bearing cast within a period of about 30 minutes to several hours. Preferably, the hardening agents are used in the compositions of the present invention in an amount such that the weight ratio of hardening agent to water-soluble silicate is at least about 1:1, and more preferably, at least about 2:1. Preferably, the hardening agents are used in the compositions of the present invention in an amount such that the ratio of hardening agent to water-soluble silicate is no greater than about 25:1, more preferably, no greater than about 10:1, even more preferably, no greater than about 5:1, and most preferably, no greater than about 3:1.

Adjuvants

The silicate-containing composition can also include effective amounts of other adjuvants such as filers, polymeric toughening agents, drying agents, binding agents, hydrophobic materials, antifoaming agents, lubricants, slip agents, stabilizers, tackifiers, pigments, dyes, and fragrances. These adjuvants may be soluble or insoluble in the composition, or covalently bound to the silicate. One or more of these adjuvants may be incorporated into the compositions of the present invention. They are each used in "an effective amount," i.e., an amount sufficient to provide one or more of the benefits of such an adjuvant, as described herein. This amount can range, for example, from about 2 weight percent to about 80 weight percent, based on the total weight of the composition.

Fillers may be used in the hardenable compositions to increase the strength and/or toughness of the cast obtained and/or reduce cost. Fillers can also be used to modify appearance and handling characteristics of the coated sheet material (i.e., the substrate coated or impregnated with the hardenable composition). Useful fillers include, but are not limited to, particulate, spherical, fibrous, microfibrous, flake, or platelet forms. The fillers may have solid, porous, or hollow structures. They may be organic or inorganic materials. Fillers may be surface treated using silanes, zirconates, titanates, etc. Examples of suitable fillers include, but are not limited to, calcium metasilicate particles and fibers (such as calcium metasilicate, also referred to as wollastonite, microfibers available under the trade designation "NYAD-G" from NYCO Minerals, Willsboro, N.Y.), calcium carbonate, calcium sulfate, kaolin, mica, talc, feldspar, barium sulfate, barium ferrite, titanium dioxide, fumed or precipitated silicas (such as those available under the trade designations "CABOSIL" TS-720 from Cabot Corp., Boyertown, Pa., or "AEROSILS" from Degussa Corp., Ridgefield Park, N.J.), insoluble amorphous and crystalline silica, ground glass, glass bubbles (such as sodium borosilicate glass bubbles, i.e., hollow glass beads, available under the trade designation "K-46" from the 3M Company, St. Paul, Minn.), glass microspheres, glass fibers, boron fibers, carbon fibers, cotton fibers, metallic fibers, ceramic fibers, ceramic particles (such as those available under the trade designations "CERAMCEL" from Microcel Tech., Inc., Edison, N.J., and "Z-LITE" from Zeelan Inc., St. Paul, Minn.), hollow ceramic spheres (such as those available under the trade designation "SIL-CELL" from Microcel Tech., Inc., Edison, N.J.), as well as particles or fibers of polyolefins, polyesters, polyamides, polyimides, polyacrylates, polycarbonates, polyurethanes, natural rubber, and the like.

The hardenable silicate-containing compositions can also include an effective amount of a polymeric toughening agent to provide effective levels of strength and toughness to the hardened composite. Suitable toughening agents preferably contain alkoxysilane functionality because hydrolysis of this adduct yields a silanol functional compound that could potentially react with the hardenable silicates of the present invention. Examples of such materials include, but are not limited to, alkoxysilane terminated polyethers (available under the trade designation "SILMODS" from Union Carbide, Danbury, Conn.); alkoxysilane polyols (prepared by mixing an epoxy terminated polyether with a bis (trimethoxysilylpropyl)amine); alkoxysilane terminated polyurethanes (as described in U.S. Pat. No. 5,423,735); alkoxysilane finctional celluloses (available from Aqualon Company, Rijswik, Netherlands); and polydimethoxysiloxane and N-octylmethyldimethoxysilane (both of which are available from Huls America, Inc., Piscataway, N.Y.). Other suitable polymeric toughening agents include isocyanate-finctional urethane prepolymers as described, for example, in U.S. Pat. Nos. 4,411,262 (vonBonin), 4,502,479 (Garwood), and 4,667,661 (Scholz et al.). If used with these prepolymers, it may be preferable to predry the water-soluble silicate before applying to the substrate.

The hardenable silicate-containing compositions can also include an effective amount of a drying agent that assists in removing water from the hardenable composition. Suitable drying agents include molecular sieves, such as zeolit molecular sieve available under the trade designation "SYLOXIV" 120 from Grace Davison Chem., Baltimore, Minn., or chemical drying agents, such as oxazolidines, which are available from Angus Chemical Co., Buffalo Grove, Ill. If a drying agent is used, it is used in an amount that shifts the equilibrium toward polymerization of the silicate with removal of water.

The hardenable silicate-containing compositions can include an effective amount of a binding agent that assists in binding the silicate(s) to the substrate, both before and after interaction with water. Binding agents, such as polyvinyl alcohol, polyvinyl acetate, and hydroxy ethyl cellulose, have been found to be particularly effective at holding the hardenable composition to the substrate during immersion in water.

In certain instances it may be desirable to control the amount of initial water uptake by treating the water-soluble silicate with a hydrophobic material For example, they can be treated with a hydrophobic silane such as N-octylmethyldimethoxysilane, which can also be used as a polymeric toughening agent to enhance physical properties. They can also be treated with a high surface area material such as hydrophobic fumed or precipitated silicas, such as those available under the trade designations "CABOSIL" TS-720 from Cabot Corp., Boyertown, Pa., or "AEROSILS" from Degussa Corp., Ridgefield Park, N.J., which can also be used as fillers.

Substrate

The hardenable casting (i.e., support) material generally comprises a substrate or scrim impregnated or coated with the hardenable silicate-containing composition. Suitable substrates include knit, woven, and nonwoven fabrics as well as rigid foams and other porous materials made of natural or synthetic fibers. Examples of preferred fiber materials that form the substrate include, but are not limited to, fiberglass, silane-treated fiberglass, nylon, polyolefins, polyamides, polyesters, cotton, rayon, and mixtures thereof Other usable materials include knits, wovens, and nonwovens, any of which may contain elastic yarns or fibers of natural rubber, synthetic rubber, or polyurethane. Preferred fabrics obtain extensibility through mechanical compaction such as microcreping or through the use of heat shrinkable highly twisted texturized yarns. Fabrics such as these are disclosed in U.S. Pat. No. 5,512,354 (Scholz et al.). The substrates may be dyed or pigmented in a solid or patterned manner, as discussed in U.S. Pat. No. 5,342,291 (Scholz et al.).

A more preferred fiber material from which stretchable casting tapes can be formed is fiberglass. Fiberglass is a high modulus fiber that contributes significant strength to the hardened orthopedic supports of the present invention. When used with a hardenable silicate-containing composition of the present invention, the combination hardens to a very hard, lightweight, strong, weight-bearing cast. While fiberglass yarns themselves are relatively inelastic, they can be knitted into a highly extensible knit fabric or substrate. Fiberglass woven or knitted substrates suitable for use in support materials according to the present invention include those used in the knitted substrate of "SCOTCHCAST" Plus casting tape, which tape is available from the 3M Company (St. Paul, Minn.). Other preferred fiberglass fabrics are those discussed in U.S. Pat. No. 4,668,563 (Buese et al.).

In general, it is desired that the orthopedic support material be constructed from a fabric or substrate which is relatively extensible and flexible; i.e., which has a lengthwise extensibility of at least about 20%, preferably about 40% to about 60%, once coated with the hardenable composition. This will facilitate fitting the support material around contoured portions of the body, such as the heel, knee or elbow. Furthermore, it is desired that the support material be constructed from a porous or mesh fabric (i.e., a fabric having apertures of sufficient size to enable water to permeate the roll of casting tape during water activation and cause the composition to harden after application to a body part or other structure). In addition, a porous fabric is desired to allow air and moisture vapor to move through the material after cure, thereby promoting patient comfort and avoiding skin breakdown caused by excessive moisture build-up under the cured material. Suitable aperture sizes are about 0.3 $mm^2$ to about 16 $mm^2$, preferably about 1.2 $mm^2$ to about 9 $mm^2$.

Non-fiberglass and low modulus substrates generally provide lower strength to the hardened orthopedic support materials. When non-fiberglass supports are used, it may be beneficial to employ glass or ceramic fillers, as described above. Preferred non-fiberglass substrates include cheese cloth gauzes and lightweight polyester knit fabrics. Other preferred non-fiberglass fabrics are disclosed in U.S. Pat. Nos. 4,841,958 (Ersfeld et al.) and 4,940,047 (Richter et al.), which are incorporated herein by reference.

To increase the adherence of the hardenable composition to the scrim and to increase the strength of the cast, various chemical treatments and/or coupling agents such as silane, titanate, or zirconate treatment of the scrim may also be included.

Preparation of Hardenable Casting Material

The hardenable silicate-containing composition can include only one or more water-soluble silicates or, preferably, it can include one or more water-soluble silicates with one or more hardening agents and/or other optional adjuvants. As purchased, a water-soluble silicate can be in the form of particulate material (typically, a finely divided powder), or a solution or a dispersion of the silicate. The hardening agent can be a liquid or a solid. If it is a liquid, the hardenable silicate-containing composition can be in the form of a moist powdered composition. Thus, the hardenable silicate-containing composition can be applied in the form of a moist particulate material desired, the hardenable silicate-containing composition can be applied to a substrate in the form of a nonaqueous slurry or a paste. Suitable nonaqueous slurries or pastes can be formed using an organic solvent, for example, isopropanol (IPA), hexamethyldisiloxane, methylene chloride, or combinations thereof Other solvents may also be used. Preferably, the organic solvents have a sufficiently high vapor pressure that they easily evaporate once the slurry or paste is applied to the substrate. This material can then be applied to a body part before or after application of water. Alternatively, an aqueous solution or dispersion of the silicate can be applied to a substrate, and then be dried after being applied to the body part.

The substrate can be coated or impregnated with the hardenable silicate-containing composition by any of a variety of means well known in the art, depending on whether the composition is in the form of a dry solid, moist solid, solution, dispersion, slurry, paste, or the like. For example, low viscosity compositions can be sprayed onto a substrate, high viscosity compositions can be applied to a substrate as a putty, and moderate viscosity compositions can be applied to a substrate by brush, knife coating, curtain coating, or with a roll coater. Compositions of the present invention may be applied at room temperature or at elevated temperature (generally less than about 100° C.).

The amount of the hardenable silicate-containing composition applied to the substrate can vary. Typically, a substrate is coated or impregnated with a hardenable silicate-containing composition in an amount of about 0.5 time to about 20 times the weight of the substrate. Preferably, this is in an amount of about 100 g/m² to about 1200 g/m², more preferably, in an amount of about 300 g/m² to about 900 g/m².

A variety of conventional techniques can be utilized to store the substrate coated or impregnated with the hardenable silicate-containing composition, prior to use to form a cast. Typically, a roll of the coated substrate of various widths, generally about 2 centimeters (cm) to about 20 cm in width, and an appropriate length will be prepared. The roll is preferably packaged within a substantially water-impermeable container such as an aluminum foil plastic laminate pouch.

Preparation of a Hardened Cast

Hardening of the coated substrate of the present invention is typically accomplished by contacting the hardenable composition with water. The composition can be hardened upon exposure to water under a variety of conditions of temperature and pressure. For example, it can harden at a temperature of about 10° C. to about 100° C., and preferably, about 20° C to about 50° C. Advantageously, however, extreme temperatures are not required. That is, the composition of the present invention advantageously can harden at about 20° C. to about 40° C.

Alternatively, hardening can occur without application of water, if water was used to apply the hardenable composition to the substrate. Simply allowing at least part of the water to evaporate can cause hardening. For example, in one embodiment, a substrate is coated or impregnated with an aqueous solution or dispersion of the hardenable silicate-containing composition, which hardens to form a hardened silicate composite upon removal of the water (as by evaporation, for example).

Orthopedic casting materials, involving the hardenable compositions of the present invention, may be applied to humans or various animals in the same fashion as other known orthopedic casting materials. First, the body part to be immobilized is preferably covered with a conventional cast padding and/or stockinet for protection. Generally, this is a protective sleeve of an air-permeable fabric such that air may pass in through the sleeve and the cast to the surface of the skin, and moisture vapor may pass out. Preferably, this sleeve does not appreciably absorb water and permits the escape of perspiration. An example of such a substrate is a knitted or woven polypropylene material The hardenable composition may be activated, for example, by dipping the orthopedic casting material in water. Excess water may then be squeezed out of the orthopedic casting material, and the material wrapped or otherwise positioned around the body part so as to properly conform thereto. Preferably, the material is then molded and smoothed to form the best fit possible and to properly immobilize the body part in the desired position. Alternatively, water that is already in the orthopedic casting material can simply be allowed to evaporate, which can activate the hardening process.

Although often not necessary, if desired, the orthopedic casting material may be held in place during hardening by wrapping an elastic bandage or other securing means around the hardening orthopedic casting material. When hardening is complete, the body part is properly immobilized within the formed orthopedic cast or splint.

The orthopedic casting material has a working time sufficient to allow the bandage to be positioned and a set time sufficient for the cast to be molded to take the shape of the body part (but short enough that the applier does not waste time). It has a hardening time sufficient for the cast to become weight-bearing. Suitable working times are about 1 minute to about 5 minutes, preferably, about 1.5 minutes to about 3 minutes. Suitable set times are about 3 minutes to about 15 minutes, preferably, about 3 minutes to about 5 minutes. Suitable hardening times are about 20 minutes to about 24 hours, preferably, about 20 minutes to about 7 hours, and more preferably, about 10 minutes to about 1 hour.

EXAMPLES

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention. All percentages used herein are based on the total weight of the hardenable composition, unless otherwise stated.

Test Methods

The following test methods were used to evaluate casting tapes made from the composition of the present invention.

Ring Compression Tests

In these tests, the "dry strength" and "wet strength" of certain cured cylindrical ring samples of the coated materials of the present invention were determined. For each of these tests, hardened cylindrical ring samples were formed by taking a roll of the coated material from its storage pouch and immersing the roll completely in deionized water having a temperature of about 23° C. for about 2 seconds to about 5 seconds. The roll of coated material was then removed from the water and the material was wrapped around a 5.08 cm mandrel covered with a thin stockinet (such as Synthetic Stockinet MS02 available from the 3M Company, St. Paul, Minn.) to form 9 complete uniform layers using a controlled wrapping tension of about 45 grams per centimeter width of the material. Each cylinder was completely wound within 30 seconds after its removal from the water.

At a point 30 minutes following the initial immersion in water, each cylinder was removed from its respective mandrel and allowed to cure for 48 hours to 60 hours in a controlled atmosphere of 34° C.±2° C. and 55%±5% relative humidity. Each cylinder was then placed in a fixture in a commercial testing instrument, e.g., an Instron instrument (Instron Corp., Park Ridge, Ill.). Compression loads were applied to the cylindrical ring sample along its exterior and parallel to its axis. The cylindrical ring was placed lengthwise between the two bottom bars of the fixture (the bars being 1.9 cm wide, 1.3 cm in height, and 15.2 cm long), with the bars spaced about 4 cm apart. The inside edges of the bars were machined to form a curved surface having a 0.31 cm radius. A third bar (0.63 cm wide, 2.5 cm high, and 15.2 cm long) was then centered over the top of the cylinder, also parallel to its axis. The bottom or contacting edge of the third bar was machined to form a curved surface having a 0.31 cm radius. The third bar was brought down to bear against and crush the cylinder at a speed of about 5 cm/minute. The maximum or peak force which was applied while crushing the cylinder was then recorded as the ring strength, which in this particular instance is the "dry strength" (expressed in terms of force per unit length of the cylinder, i.e., newtons/centimeter or N/cm). The average peak force applied was then calculated and reported as the "dry strength."

To measure the "wet strength," the same procedure was followed as for the "dry strength," except that after curing for 48 hours to 60 hours, the cylinder was immersed in water at about 25° C. for about 30 minutes. The cylinder was then placed in the instrument and crushed as described hereinabove in order to determine the "wet strength" thereof
Compression 3-Point Bend Test Method Each splint sample was placed between two curved support bars (0.9 cm radius, 13.6 cm in length) of the test fixture of the Instron instrument described above with the bars spaced about 5.7 cm apart. A third curved bar (0.9 cm radius, 13.6 cm in length) was centered over the top of the support bars and was brought down to bear against and crush the splint sample at a speed of 5 cm/minute. The maximum or peak force which was applied while crushing the splint was then recorded as the splint strength in Newtons/cm.

Example 1

The feasibility of preparing a hardened article by adding water to a water-soluble silicate and an allylene carbonate hardening agent was demonstrated in this example.

A soluble sodium silicate (available under the trade designation "BRITESIL" C24 sodium silicate having a weight ratio of $SiO_2/Na_2O$ of 2.4/1 from PQ Corp., Valley Forge, Pa.) and propylene carbonate (available from Aldrich Chemical, Milwaukee, Wis.) were combined to form a hardenable silicate-containing composition. This composition was in the form of a moist powdered material containing 71 percent by weight of the sodium silicate and 29 percent by weight of the propylene carbonate. Water was added with gentle stirring to the hardenable silicate-containing composition to form a mixture containing 42 percent by weight water, based on the total weight of the composition plus water. The resulting mixture gelled in 20 seconds and then quickly hardened to give a hardened silicate-containing composition.

Example 2–6

The feasibility of preparing hardened articles by adding water to a water-soluble silicate and a variety of different hardening agents was demonstrated in Example 2–6.

Several hardenable silicate-containing compositions were prepared by combining a soluble sodium silicate ("BRITESIL" C24 sodium silicate having a tio of $SiO_2/Na_2O$ of 2.4/1, PQ Corp., Valley Forge, Pa.) with different agents to give hardenable silicate-containing compositions as listed in

TABLE 1

| Example | Silicate Ingredient | Wt % | Hardening Agents | Wt % |
|---|---|---|---|---|
| 2 | "BRITESIL" C24 Sodium Silicate | 91 | Triacetin (Glycerol Triacetate) (Eastman Chem., Kingport, TN) | 9 |
| 3 | "BRITESIL" C24 Sodium Silicate | 75 | Succinic Anhydride (Aldrich Chem., Milwaukee, WI) | 25 |
| 4 | "BRITESIL" C24 Sodium Silicate | 60 | Sodium Bicarbonate (Aldrich Chem., Milwaukee, WI) | 40 |
| 5 | "BRITESIL" C24 Sodium Silicate | 75 | "GANTREZ" AN-139 Methyl Vinyl Ether/Maleic Anhydride Copolymer) (International Specialty Products, Lambard, IL) | 25 |
| 6 | "BRITESIL" C24 Sodium Silicate | 56 | Propylene Carbonate (Aldrich Chem., Milwaukee, WI) Citric Acid (Aldrich Chem., Milwaukee, WI) | 33 11 |

Independent experiments, the compositions of Examples 2–6 were mixed oden spatula for 15 seconds. Examples 2 and 6 were moist powdered and Examples 3, 4, and 5 were dry powdered materials. Water was then added with gentle stirling in amounts shown in Table 2 (percentages are based on the total weight of the composition plus water). The mixtures all gelled within a short period of time and then hardened into a solid as indicated in Table 2.

TABLE 2

| Example | Added Water (% By Weight) | Observed Results |
|---|---|---|
| 2 | 48 | Mixture gelled in 10 minutes and then hardened to a brittle solid after 30 hours. |
| 3 | 50 | Mixture gelled in 30 seconds and hardened to a brittle solid in 5 minutes |
| 4 | 44 | Mixture gelled within 1 minute and quickly hardened into a brittle solid. |
| 5 | 50 | Mixture gelled within 2 minutes and hardened into a tough solid in 30 minutes. |
| 6 | 36 | Mixture gelled in 5 minutes and hardened to a brittle solid within 15 minutes. The pH of the excess liquid was found to be about 7. |

The results of this example show that useful hardening agents can be selected from classes of compounds including acids, esters, anhydrides, polymeric anhydrides, bicarbonates, and mixtures thereof (e.g., alkylene carbonates and carboxylic acids).

Example 7

The feasibility of preparing a casting article by adding water to a fiberglass substrate containing a water-soluble silicate and an alkylene carbonate hardening agent was demonstrated in this example.

A soluble sodium silicate ("GD" sodium silicate having a weight ratio of $SiO_2/Na_2O$ of 2.0/1, PQ Corp., Valley Forge, Pa.) and propylene carbonate (Aldrich Chemical, Miwaukee, Wis.) were combined to form a hardenable silicate-containing composition. This composition was in the form of a moist powdered material containing 71 percent by weight of the sodium silicate and 29 percent by weight of the propylene carbonate.

Isopropanol (IPA) was added to the hardenable silicate-containing composition in sufficient quantity to make a coatable slurry with low viscosity. The resulting slurry was coated onto an open mesh (aperture size about 1.5 mm×3.0 mm) knit fiberglass yarn (7.62 cm×200 cm) by pouring the slurry over the fabric and distributing the material evenly with a wooden spatula After allowing the IPA to evaporate over a period of 2 hours, the coated fabric was rolled around a plastic core and stored in an aluminum foil pouch. The roll (casting tape) was dipped for about 2 seconds in water (23° C.) and wound around a 5.08-cm diameter mandrel to make a 9-layer ring. The casting tape was sufficiently creamy and easily molded to make a ring with good lamination. After drying for 24 hours, the ring was found to weigh 125 grams. The ring compression strength was measured on an Instron machine and found to be 54.2 N/cm width. This demonstrates that a casting article of good compression strength can be made by utilizing a knit fiberglass fabric coated with a hardenable composition containing sodium silicate and a propylene carbonate hardening agent.

Example 8

The feasibility of preparing silicate-based casting articles with added fillers and drying agents was demonstrated in this example.

A soluble sodium silicate ("GD" sodium silicate having a weight ratio of $SiO_2/Na_2O$ of 2.0/1, PQ Corp., Valley Forge, Pa.), a 50:50 mixture of propylene carbonate and ethylene carbonate (available under the trade designation "JEFF-SOL" EC-50 from Hunstman Corp., Houston, Tex.), glass bubbles (a filler available under the trade designation "K-46" from the 3M Company, St. Paul Minn.), calcium metasilicate microfibers (a filler available under the trade designation "NYAD-G" from NYCO Minerals, Wlisboro, N.Y.), and 4-Angstrom activated and predried zeolit molecular sieve (a drying agent available under the trade designation "SYLOXIV" 120 from Grace Davison Chem., Baltimore, Minn.) were combined to form a hardenable silicate-containing composition. This composition was a moist powdered material due to the presence of the liquid carbonates. It contained 48 percent by weight of the sodium silicate, 22 percent by weight of the carbonate mixture, 15 percent by weight of the glass bubbles, 7 percent by weight of the microfibers, and 7 percent by weight of the molecular sieve.

This moist hardenable silicate-containing composition was coated onto a cheesecloth substrate (7.6 cm×200 cm; 9.1×7.9 openings per cm) by pressing the material into the substrate by hand. A wooden spatula was used to smooth the surface of the impregnated substrate while removing excess material. The impregnated substrate was then rolled around a plastic core and stored in an aluminum foil pouch.

The roll (casting tape) was dipped into water (25° C.) for about 2 seconds and wound around a 5.08-cm diameter mandrel to form a 9-layer ring (casting article). The casting tape could be easily wound and was sufficiently creamy and moldable to make a ring with a smooth surface. The ring became rigid in 3 minutes and, after drying for 24 hours, it was weighed and ring compression strength was measured. This same procedure was repeated to make several rings. The results of compression strength measurements are listed in Table 3.

TABLE 3

| Ring Number | Weight (grams) | Ring Compression Strength (N/cm Width) |
| --- | --- | --- |
| 1 | 63 | 40.3 |
| 2 | 67 | 45.0 |

TABLE 3-continued

| Ring Number | Weight (grams) | Ring Compression Strength (N/cm Width) |
| --- | --- | --- |
| 3 | 72 | 50.8 |
| 4 | 67 | 45.8 |

The results of this example show that a very moldable, easy-to-apply casting tape can be made by utilizing a cheesecloth fabric coated with a water-soluble sodium silicate and an alkylene carbonate hardening agent, plus added fillers and a drying agent. The resultant hardened articles had good compression strength; however, when compared to the hardened article of Example 7, which utilized a knit fiberglass substrate, the compression strengths were not as high Example 9 and Comparative Example A A comparison of the ring compression strengths of dry and wet casting articles made from a silicate-containing hardenable support material of the present invention and standard, commercial plaster of Paris is provided in this example.

A soluble sodium silicate (available under the trade designation "GD" sodium silicate having a weight ratio of $SiO_2/Na_2O$ of 2.0/1 from PQ Corp., Valley Forge, Pa.), propylene carbonate (available under the trade designation "JEFFSOL" PC from Hunstman Corp., Houston, Tex.), glass bubbles (a filler available under the trade designation "K-46" from the 3M Company, St. Paul, Minn.), calcium metasilicate microfibers (a filler available under the trade designation "NYAD-G" from NYCO Minerals, Willsboro, N.Y.), and isopropanol (IPA.) were combined to form a hardenable silicate-containing composition This hardenable composition was stirred with a plastic spatula and shaken by hand to make a homogeneous slurry. It contained 34 percent by weight of the sodium silicate, 15 percent by weight of the propylene carbonate, 11 percent by weight of the glass bubbles, 11 percent by weight of the microfibers, and 29 percent by weight of the IPA "A piece of cheesecloth substrate (7.6 cm×200 cm; 9.1× 7.9 openings per cm) was fed between a knife and bed of a steel knife coater with the knife set at a gap of 0.064 cm.

A portion of the slurry was quickly poured onto a small portion of the substrate behind the knife and the substrate was coated by pulling it through the knife gap. This procedure was repeated to make a total of six sheets (samples R1–R6). After allowing the IPA to evaporate over a period of 2 hours, each sample was rolled around a plastic core and stored in an aluminum foil pouch. The rolls (casting tapes) were dipped in water (23° C.) for 2 seconds and each wound around a mandrel to give a 9-layer ring (casting article). Six 9-layer rings of plaster of Paris (POP) (Johnson & Johnson Extra-Fast Setting, 7.63 cm×300 cm, casting tape) were also made (samples POP1–POP6). After drying for 40 hours, the rings were weighed and ring compression strengths of 6 of the 12 rings were measured. The other six rings were submerged in water (25° C.) for 30 minutes and ring compression strengths measured. The results are listed in Table 4.

TABLE 4

| Ring Number | Ring Type | Dry or Wet When Tested | Weight (grams) | Ring Compression Strength (N/cm Width) |
|---|---|---|---|---|
| R1 | Silicate | Dry | 50 | 40.5 |
| R2 | Silicate | Dry | 45 | 39.8 |
| R3 | Silicate | Dry | 41 | 30.8 |
| POP1 | POP | Dry | 70 | 72.6 |
| POP2 | POP | Dry | 66 | 72.3 |
| POP3 | POP | Dry | 63 | 64.1 |
| R4 | Silicate | Wet | 46 | 25.8 |
| R5 | Silicate | Wet | 45 | 22.3 |
| R6 | Silicate | Wet | 43 | 13.2 |
| POP4 | POP | Wet | 62 | 20.3 |
| POP5 | POP | Wet | 66 | 20.5 |
| POP6 | POP | Wet | 66 | 22.5 |

From these results, it can be concluded that the ring compression strength of casting articles made from silicate-containing materials of this invention is reduced much less upon wetting than comparable casting articles made from plaster of Paris.

Example 10

The feasibility of preparing a splint by adding water to a fiberglass substrate containing a water-soluble silicate, an allylene carbonate hardening agent and a polymeric toughening agent was demonstrated in this example.

A soluble sodium silicate (available under the trade designation "BRITESIL" C24 sodium silicate having a weight ratio of $SiO_2/Na_2O$ of 2.4/1 from PQ Corp., Valley Forge, Pa.), propylene carbonate (available from Aldrich Chemical, Milwaukee, Wis.), glass bubbles (a filler available under the trade designation "K-46" from the 3M Company, St. Paul, Minn.), calcium metasilicate microfibers (a filler available under the trade designation "NYAD-G" from NYCO Minerals, Willsboro, N.Y.), and a silyl polyol (a polymeric toughening agent) were combined to form a hardenable silicate-containing composition. The silyl polyol was prepared by mixing 48 percent by weight of an epoxy terminated polyether (available under the trade designation "DER 732" from Dow Chemical, Midland, Mich.) and 52 percent by weight of a bis(trimethoxysilylpropyl)amine (available under the trade designation "A-1170" from Union Carbide, Danbury, Conn.) for six days and then heating at 70° C. for 12 hours. The hardenable composition contained 45 percent by weight of the sodium silicate, 21 percent by weight of the propylene carbonate, 14 percent by weight of the glass bubbles, 14 percent by weight of the microfibers, and 5 percent by weight of the silyl polyol.

This composition was in the form of a moist powdered material. It was coated onto two pieces of knit fiberglass substrate (7.62 cm×200 cm) as described in Example 7. The impregnated fiberglass substrates were fanfolded into two 8-layer splints of about 20-cm in length. The splint materials were then quickly dipped in water (23° C.) and allowed to dry and harden over 24 hours under ambient conditions. The splints were then compressed in a 3-point bend test with an Instron machine, as described above. The average maximum force obtained for the two samples was 54 N/cm width.

The results of this example show that an easy-to-apply splint material can be made by utilizing a knit fiberglass fabric coated with a water-soluble sodium silicate and propylene carbonate hardening agent plus added fillers and a polymeric diluent.

Example 11 and Comparative Example B

A comparison of the moisture vapor transmission rate (MVTR) of casting articles made from a silicate-based material and standard, commercial plaster of Paris casts is provided in this example.

A soluble sodium silicate (available under the trade designation "GD" sodium silicate having a weight ratio of $SiO_2/Na_2O$ of 2.0/1, PQ Corp., Valley Forge, Pa.), a 50:50 mixture of propylene carbonate and ethylene carbonate (available under the trade designation "JEFFSOL" EC-50 from Hunstrnan Corp., Houston, Tex.), glass bubbles (a filer available under the trade designation "K-46" from the 3M Company, St. Paul, Minn.) were combined to form a hardenable silicate-containing composition. This composition was in the form of a moist powdered material containing 42 percent by weight of the sodium silicate, 14 percent by weight of the carbonate mixture, and 44 percent by weight of the glass bubbles.

A 50:50 mixture of isopropanol (IPA) and hexamethyldisiloxane was added to the hardenable silicate-containing composition in sufficient quantity to make a coatable slurry with low viscosity. The resulting slurry was coated onto three 7.6 cm×3 m pieces of a lightweight polyester non-woven fabric (20 $g/m^2$) and the solvent allowed to evaporate over a period of 1.5 hours.

After allowing the solvent mixture to evaporate, the coated fabric was rolled around a plastic core to make three rolls of casting tape. The rolls were immersed for about 2 seconds in water (23° C.) and wound around a 5.08-cm diameter mandrel to make three 9-layer rings (Samples R1–R3). Two 9-layer rings of plaster of Paris (Johnson & Johnson Extra-Fast Setting, 7.63 cm×300 cm, casting tape) were also made (Samples POP1 and POP2). The rings were allowed to dry for several days.

The rings were then sealed on one side with plastic petri dishes and silicone sealant, a 50-ml beaker filled with 30 ml of deionized water was placed in the center of the rings, and the top of the rings were sealed with petri dishes and silicone sealant. The samples were allowed to equilibrate for 6 days at 24° C. and 50% relative humidity and then weighed. After 3 days, the samples were weighed again and the amount of water loss through the rings (grams and MVTR) was calculated. The physical dimensions of the rings and the calculated water loss and MVTR results are provided in Table 5.

TABLE 5

| Ring Number | Ring Thickness (cm) | Ring Height (cm) | Water Loss (grams) | MVTR ($g/m^2/day$) |
|---|---|---|---|---|
| R1 | 0.58 | 7.1 | 2.4 | 70 |
| R2 | 0.46 | 7.2 | 2.0 | 57 |
| R3 | 0.53 | 7.4 | 1.8 | 51 |
| POP1 | 0.58 | 7.3 | 2.0 | 57 |
| POP2 | 0.53 | 7.4 | 1.7 | 48 |

The results of this example show that the water loss and MVTR of hardened silicate orthopedic casts of the present invention are very similar to traditional plaster of Paris cast materials.

Example 12

The feasibility of preparing a casting article by allowing water to evaporate from a fiberglass substrate coated with an aqueous solution of a hardenable silicate plus added fillers was demonstrated in this example.

An aqueous sodium silicate solution (available under the trade designation "TEX-SIL" BP-42 sodium silicate solution, 45% solids, Chemical Products Corp., Cartersville, Ga.), calcium metasilicate microfibers (a filler available under the trade designation "NYAD-G" from NYCO Minerals, Willsboro, N.Y.), and hollow ceramic spheres (a filler available under the trade designation "SIL-CELL" 35/34 from Silbrico Corp., Hodgkins, Ill.) were combined to form a hardenable silicate-containing composition. This hardenable composition was stirred with a plastic spatula and shaken by hand to make a homogeneous slurry. It contained 78 percent by weight of the aqueous sodium silicate solution, 16 percent by weight of the microfibers, and 6 percent by weight of the hollow ceramic spheres.

This slurry was coated onto an open weave fiberglass substrate (7.6 cm×200 cm) as described in Example 7. The sample was allowed to partially dry for 2 hours under ambient conditions, rolled around a plastic core, and stored in a foil pouch. The roll was subsequently removed from the pouch and wound around a 5.08-cm diameter mandrel to make a 20-cm long cast. After 48 hours, the cast was rigid.

The results of this example show that a rigid casting material can be made by removing water, e.g., through evaporation, from a knit fiberglass substrate coated with an aqueous sodium silicate solution plus added fillers.

Example 13

In a dry room kept at less than 5% relative humidity, 316 grams of an isocyanate functional urethane prepolymer, the components of which are described in Table 6 below, 70 grams of expanded perite "SIL-CELL" 35/34, and 100 grams of sodium silicate "GD" (PQ Corp., Valley Forge, Pa.) that had been previously dried at 121° C. for 72 hours were added to a 1 quart glass jar. The mixture was shaken and mixed by hand with a rubber spatula until it became homogeneous. A 7.6 cm×3 m piece of a polyester knit substrate (42 g/m$^2$) was fed between a knife and bed of a steel knife coater with the knife set at a gap of 0.031 cm. The hardenable composition was poured onto a small portion of the scrim behind the knife and the scrim was coated with the hardenable composite at 218 g/m$^2$ by pulling it through the knife gap at a rate of approximately 15 cm/second. The coated article was rolled around a plastic core and stored in a moisture impervious aluminum foil pouch.

TABLE 6

| Isocyanate Functional Urethane Prepolymer | | |
|---|---|---|
| Component | Weight Percent | Grams |
| "ISONATE" 2143L (diphenylmethane diisoyanate) (Dow Chemical) | 61.3 | 194 |
| Benzoyl chloride (Aldrich) | 0.06 | 0.2 |
| Butylated hydroxy tolune (BHT, Aldrich) | 0.48 | 1.52 |
| DB-100 (Dow Corning, Midland, MI) | 0.18 | 0.57 |
| Dimorpholinodiethylether (Huntsman Corp.) | 1.2 | 3.8 |
| "CARBOWAX" 1000 (polyethylene glycol) (Union Carbide) | 12.9 | 40.7 |
| "CARBOWAX" 1450 (polyethylene glycol) (Union Carbide) | 12.9 | 40.7 |
| "ARCOL" LG-650 (polypropylene triol) (Arco, Newtown Square, PA) | 7.0 | 22 |
| "PLURONIC" F-108 (polyethylene polypropylene block copolymer) (BASF, Wyandotte, MI) | 4.0 | 12.6 |

The next day, the roll was removed from the pouch, charged with water at 23° C., and rolled around a 5.08 cm diameter mandrel to make a nine layer ring that became rigid within 5 minutes. After a 24 hour period, the ring was tested under compression to yield a maximum crush strength of 51 N/cm.

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An orthopedic support material comprising a substrate and a hardenable composition comprising a water-soluble silicate, wherein at least about 1 part of the water-soluble silicate is soluble in about 6 parts water at 25° C., and further wherein the substrate and hardenable composition form an orthopedic support material.

2. The orthopedic support material of claim 1, wherein at least about 1 part of the water-soluble silicate dissolves in about 6 parts water at 25° C. in less than about 20 minutes.

3. The orthopedic support material of claim 2, wherein at least about 1 part of the water-soluble silicate dissolves in about 6 parts water at 25° C. in less than about 5 minutes.

4. The orthopedic support material of claim 1, wherein the water-soluble silicate has the formula $SiO_2/M_2O$ wherein M is Li, Na, K, or $NR_4$, wherein each R is independently hydrogen or a $(C_1-C_{10})$organic group.

5. The orthopedic support material of claim 4, wherein each R is independently hydrogen or an organic group selected from the group of an alkyl group, an aryl group, an aralkyl group, and an alkaryl group.

6. The orthopedic support material of claim 5, wherein each R is independently hydrogen or an organic group selected from the group of an alkyl moiety, an alkyl group interrupted with one or more O, N, or S atoms, a hydroxyalkyl group, an aryl group, an aralkyl group, and an alkaryl group.

7. The orthopedic support material of claim 4, wherein the weight ratio of $SiO_2$ to $M_2O$ is within a range of about 0.20/1 to about 20/1.

8. The orthopedic support material of claim 5, wherein the weight ratio of $SiO_2$ to $M_2O$ is within a range of about 1/1 to about 10/1.

9. The orthopedic support material of claim 4, wherein the weight ratio of $SiO_2$ to $M_2O$ is within a range of about 1.6/1 to about 3.3/1.

10. The orthopedic support material of claim 1, wherein the hardenable composition further comprises a hardening agent.

11. The orthopedic support material of claim 10, wherein the hardening agent is selected from the group of inorganic acids, organic acids, esters, anhydrides, alkylene carbonates, and salts, derivatives, and mixtures thereof.

12. The orthopedic support material of claim 11 wherein the hardening agent is an alkylene carbonate.

13. The orthopedic support material of claim 10, wherein the hardenable composition further comprises an adjuvant selected from the group of a filler, a polymeric toughening agent, a drying agent, and mixtures thereof.

14. The orthopedic support material of claim 10, wherein the substrate is selected from the group of knit fabric, woven fabric, nonwoven fabric, and rigid foam.

15. The orthopedic support material of claim 10, wherein the substrate is coated or impregnated with the hardenable silicate-containing composition in an amount of about 0.5 time to about 20 times the weight of the substrate.

16. An orthopedic support material comprising a substrate and a hardenable composition consisting essentially of a water-soluble silicate, wherein at least about 1 part of the water-soluble silicate is soluble in about 6 parts water at 25° C.

17. The orthopedic support material of claim 16, wherein the water-soluble silicate has the formula: $SiO_2/M_2O$ wherein M is Li, Na, K, or $NR_4$, wherein each R is independently hydrogen or a ($C_1$–$C_{10}$)organic group.

18. An orthopedic support material comprising a substrate and a hardenable composition comprising:
   a water-soluble silicate having the formula $SiO_2/M_2O$ wherein M is Li, Na, K, or $NR_4$, wherein each R is independently hydrogen or a ($C_1$–$C_{10}$)organic group, and wherein at least about 1 part of the water-soluble silicate is soluble in about 6 parts water at 25° C.; and
   a hardening agent; wherein the substrate and hardenable composition form an orthopedic support material.

19. The orthopedic support material of claim 18, wherein each R is independently hydrogen or an organic group selected from the group of an alkyl group, an aryl group, an aralkyl group, and an alkaryl group.

20. A method of preparing an orthopedic support material comprising:
   providing a substrate;
   applying a hardenable composition comprising a water-soluble silicate to the substrate, wherein at least about 1 part of the water-soluble silicate is soluble in about 6 parts water at 25° C.; and
   allowing the hardenable composition to harden.

21. The method of claim 20, wherein the hardenable composition further comprises a hardening agent.

22. The method of claim 20, wherein the hardenable composition includes an organic solvent when applied to the substrate.

23. The method of claim 20, wherein the hardenable composition includes water when applied to the substrate.

24. An orthopedic support material prepared by the method of claim 20.

25. A method of immobilizing a body part, the method comprising:
   providing an orthopedic support material comprising a substrate and a hardenable composition comprising a water-soluble silicate, wherein at least about 1 part of the water-soluble silicate is soluble in about 6 parts water at 25° C.;
   applying the orthopedic support material to a body part;
   applying water to the orthopedic support material; and
   allowing the hardenable composition to harden.

26. The method of claim 25, wherein the hardenable composition further comprises a hardening agent.

27. The method of claim 25, wherein the step of applying water to the orthopedic support material occurs prior to the step of applying the orthopedic support material to a body part.

28. A method of immobilizing a body part, the method comprising:
   providing an orthopedic support material comprising a substrate and a hardenable composition comprising water and a water-soluble silicate, wherein at least about 1 part of the water-soluble silicate is soluble in about 6 parts water at 25° C.;
   applying the orthopedic support material to a body part; and
   removing at least part of the water from the orthopedic support material to harden the hardenable composition.

29. The method of claim 27, wherein the hardenable composition further comprises a hardening agent.

* * * * *